United States Patent
Amans (10) Patent No.: US 11,241,323 B2
(45) Date of Patent: Feb. 8, 2022

(54) CEREBRAL BLOOD FLOW REORGANIZATION

(71) Applicant: The Regents of the University of California, Oakland, CA (US)

(72) Inventor: Matthew Amans, San Francisco, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 187 days.

(21) Appl. No.: 16/468,530

(22) PCT Filed: Dec. 14, 2017

(86) PCT No.: PCT/US2017/066248
§ 371 (c)(1),
(2) Date: Jun. 11, 2019

(87) PCT Pub. No.: WO2018/112118
PCT Pub. Date: Jun. 21, 2018

(65) Prior Publication Data
US 2020/0069410 A1 Mar. 5, 2020

Related U.S. Application Data

(60) Provisional application No. 62/434,116, filed on Dec. 14, 2016.

(51) Int. Cl.
*A61F 2/90* (2013.01)
*A61F 2/06* (2013.01)
(Continued)

(52) U.S. Cl.
CPC ............. *A61F 2/90* (2013.01); *A61F 2/01* (2013.01); *A61F 2/012* (2020.05); *A61F 2/06* (2013.01);
(Continued)

(58) Field of Classification Search
CPC ............. A61F 2/012; A61F 2002/068; A61F 2002/823; A61F 2002/826; A61F 2/852; A61F 2/86; A61F 2/90
See application file for complete search history.

(56) References Cited

U.S. PATENT DOCUMENTS 8,099,156 B1 1/2012 Schnitzer et al.
2002/0193827 A1 12/2002 McGuckin et al.
(Continued)

FOREIGN PATENT DOCUMENTS

EP 2837361 A1 2/2015
WO 2008073964 A2 6/2008

OTHER PUBLICATIONS

European Examination Report dated May 7, 2021 issued in corresponding EP Appln. No. 17 882 094.0.
(Continued)

*Primary Examiner* — Suba Ganesan
(74) *Attorney, Agent, or Firm* — Carter, DeLuca & Farrell LLP (57) ABSTRACT

An implantable device includes an outer tubular member defining a longitudinal axis and a lumen. The outer tubular member includes: an outer wall portion having a plurality of first strands defining a plurality of first openings therebetween, the outer wall portion having a first porosity; and an inner baffle portion disposed within the lumen, the inner baffle portion including a plurality of second strands defining a plurality of second openings therebetween, the inner baffle portion having a second porosity that is lower than the first porosity of the outer wall portion.

7 Claims, 10 Drawing Sheets

(51) Int. Cl.
   *A61F 2/01* (2006.01)
   *A61F 2/86* (2013.01)
   *A61B 5/026* (2006.01)
   *A61F 2/82* (2013.01)
   *A61F 2/852* (2013.01)

(52) U.S. Cl.
   CPC .............. *A61F 2/86* (2013.01); *A61B 5/0263* (2013.01); *A61F 2/852* (2013.01); *A61F 2002/068* (2013.01); *A61F 2002/823* (2013.01); *A61F 2002/826* (2013.01); *A61F 2250/0004* (2013.01); *A61F 2250/0023* (2013.01)

(56) References Cited

U.S. PATENT DOCUMENTS

| | | | |
|---|---|---|---|
| 2004/0010308 A1* | 1/2004 | Zafrir-Pachter | A61F 2/82 623/1.35 |
| 2004/0138736 A1* | 7/2004 | Obara | A61F 2/91 623/1.16 |
| 2006/0155322 A1 | 7/2006 | Sater et al. | |
| 2009/0105747 A1 | 4/2009 | Chanduszko et al. | |
| 2010/0160779 A1 | 6/2010 | Browning et al. | |
| 2012/0277787 A1 | 11/2012 | Eggers | |
| 2013/0191100 A1 | 7/2013 | Mihalef et al. | |
| 2014/0039535 A1 | 2/2014 | Eskuri | |
| 2015/0216684 A1 | 8/2015 | Enzmann et al. | |
| 2017/0189217 A1* | 7/2017 | Folan | A61F 2/852 |

OTHER PUBLICATIONS

The extended European Search Report issued in corresponding Appl. No. EP 17882094.0 dated Jul. 29, 2020 (6 pages).

The International Search Report and Written Opinion dated Mar. 5, 2018 issued in corresponding PCT Appln. No. PCT/US2017/066248.

* cited by examiner

CEREBRAL BLOOD FLOW REORGANIZATION

CROSS REFERENCE TO RELATED APPLICATIONS

The present application is a National Stage Application under 35 U.S.C. § 371(a) of PCT/US2017/66248, filed Dec. 14, 2017, which claims the benefit of and priority to U.S. Provisional Patent Application Ser. No. 62/434,116, filed Dec. 14, 2016. The entire disclosures of all of the foregoing applier which is incorporated by reference herein.

BACKGROUND

Tinnitus is an auditory perception of sound in the absence of an external source. Tinnitus affects more than 50 million Americans. The impact of tinnitus is high, due to the cost of diagnosing and treating tinnitus as well as the high levels of comorbid debilitating psychiatric illnesses associated with tinnitus. Lives of patients suffering from tinnitus can be severely impacted, and it is not uncommon for patients to suffer from insomnia, depression, or even have suicidal ideations.

Tinnitus may be pulsatile and non-pulsatile. Although difficult to treat, non-pulsatile tinnitus may be treated using deep brain stimulation ("DBS") and transcranial magnetic stimulation ("TMS"). Pulsatile tinnitus is rhythmic and accounts for about 10% of tinnitus patients. Pulsatile tinnitus may be just as debilitating as non-pulsatile tinnitus. There are many causes of pulsatile tinnitus, but the common mechanism of sound generation is attributed to flow patterns in blood vessels near the cochlea, the sound sensing cavity of the inner ear. In particular, pulsatile tinnitus may be caused by abnormal pulse-synchronous blood flow in vascular structures disposed near the cochlea, such as, transverse sinus, sigmoid sinus and internal jugular vein ("SSIJ"). The vascular structures with abnormal flow may be either venous or arterial. Approximately 40% of pulsatile tinnitus etiologies are due to abnormal venous flow, approximately 35% are due to arterial abnormalities, with the remainder of the cases being unidentified.

Unfortunately, not all cases of pulsatile tinnitus are treatable. In addition, the risks of conventional pulsatile tinnitus treatments may be greater than the risks of the underlying disease. Conventional pulsatile tinnitus treatments include endovascular or open surgical occlusion of a laterally-projecting out-pouching from the sigmoid sinus, termed a diverticulum. Other treatment options include open surgical resurfacing of the sinus, which has a risk of postoperative complications as high as 23% and may result in venous sinus thrombosis, which could lead to intracranial hemorrhage, facial swelling, and wound dehiscence. Thus, therapeutic options may be more dangerous than the underlying disease, especially when the disease carries essentially no risk of stroke or hemorrhage. Accordingly, there is a need for improved treatment methods and devices for treating pulsatile tinnitus.

SUMMARY

The present disclosure provides a method and implantable device for treating pulsatile tinnitus. The method includes imaging cerebral blood vessels, in particular those adjacent the cochlea to evaluate blood flow in patients with suspected venous etiology. Flow irregularities in the SSIJ are believed to be responsible for pulsatile tinnitus. Thus, imaging these blood vessels allows for identification of an irregular flow pattern having a strong vortex or lateral flow component in the internal jugular vein at the junction with the sigmoid sinus. The vortex flow pattern is believed to be responsible for sound generation for both venous etiologies of pulsatile tinnitus and patients without a previously identified venous etiology. As such, up to 65% of pulsatile tinnitus may be a caused by this vortex flow pattern in the SSIJ. The method according to the present disclosure also includes implanting a device in the cerebral venous sinuses that disrupts the vortex flow pattern in the SSIJ, thus, removing the sound generation associated with the blood flow.

The present disclosure also provides a device configured to be implanted in a blood vessel to disrupt a vortex flow pattern while minimizing effect on the longitudinal flow through the blood vessel. The device may be implanted transluminally within a portion of the blood vessel having the vortex flow. The device includes an outer wall defining a lumen and one or more baffles disposed within the lumen. The location of the baffle within the lumen interrupts the vortex flow pattern.

According to one embodiment of the present disclosure, an implantable device is provided. The implantable device includes: an outer tubular member defining a longitudinal axis and a lumen, the outer tubular member having: an outer wall portion having a plurality of first strands defining a plurality of first openings therebetween, the outer wall portion having a first porosity. The implantable device also includes an inner baffle portion disposed within the lumen, the inner baffle portion including a plurality of second strands defining a plurality of second openings therebetween, the inner baffle portion having a second porosity that is lower than the first porosity of the outer wall portion.

According to one aspect of the above embodiment, the inner baffle portion may include a planar surface.

According to another aspect of the above embodiment, the inner baffle portion may include an inner tubular member. The inner tubular member of the inner baffle portion is eccentric relative to the outer tubular member. The implantable device may further include a wire coupled to the inner tubular member, wherein movement of the wire adjusts the second porosity of the inner baffle member.

According to a further aspect of the above embodiment, at least one of the first porosity and the second porosity are adjustable.

According to another embodiment of the present disclosure, a method for treating pulsatile tinnitus is provided. The method includes: imaging cerebral blood vessels adjacent cochlea to identify irregular blood flow having a rotational flow component; and implanting an implantable device into a jugular vein. The implantable device includes: an outer tubular member defining a longitudinal axis and a lumen, the outer tubular member having an outer wall portion having a plurality of first strands defining a plurality of first openings therebetween, the outer wall portion having a first porosity. The implantable device also includes an inner baffle portion disposed within the lumen, the inner baffle portion including a plurality of second strands defining a plurality of second openings therebetween, the inner baffle portion having a second porosity that is lower than the first porosity of the outer wall portion, wherein the inner baffle portion is configured to disrupt the rotational flow component.

According to one aspect of the above embodiment, the inner baffle portion may include an inner tubular member. The method may further include adjusting a diameter of the inner tubular member to adjust the second porosity of the inner baffle portion.

According to a further embodiment of the present disclosure, a method for treating pulsatile tinnitus is provided. The method includes: imaging cerebral blood vessels adjacent cochlea to identify irregular blood flow having a rotational flow component; and implanting an implantable device into at least one of a jugular bulb or a jugular vein to disrupt the rotational flow component.

According to one aspect of the above embodiment, the implantable device may include a tubular member defining a longitudinal axis and a lumen, the tubular member having an outer wall portion having a plurality of first strands defining a plurality of first openings therebetween, the outer wall portion having a first porosity.

According to another aspect of the above embodiment, the implantable device further includes: an inner baffle portion disposed within the lumen, the inner baffle portion including a plurality of second strands defining a plurality of second openings therebetween, the inner baffle portion having a second porosity that is lower than the first porosity of the outer wall portion.

According to a further aspect of the above embodiment, the implantable device includes a plurality of tubular members. The plurality of tubular members may be arranged in a stacked configuration, such that each of the tubular members is arranged in parallel relative to each other. The plurality of tubular members may be disposed in a grid pattern.

According to yet another aspect of the above embodiment, the tubular member is at least one of a stent or a stent strut.

BRIEF DESCRIPTION OF THE DRAWINGS

Embodiments of the present disclosure are described herein with reference to the accompanying drawings, wherein.

DETAILED DESCRIPTION

Embodiments of the present disclosure are described in detail with reference to the drawings, in which like reference numerals designate identical or corresponding elements in each of the several views. As used herein the term "proximal" refers to the portion of an implantable device that is closer to a delivery device, while the term "distal" refers to the portion that is farther from the delivery device.

Figure 1:
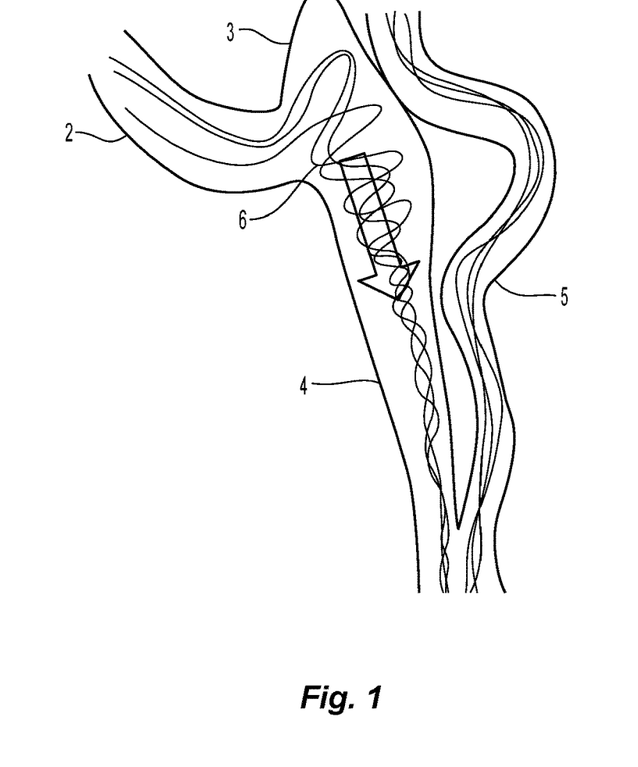
FIG. 1 is a three-dimensional time-resolved magnetic resonance velocimetry image of blood flow through a sigmoid sinus and a jugular vein.

FIG. 1 shows a velocimetry image of irregular blood flow through SSIJ of a patient suffering from pulsatile tinnitus. In particular, FIG. 1 shows a sigmoid sinus 2, a jugular bulb 3, a jugular vein 4, and a carotid artery 5, and blood flow 6 through the jugular vein 4. More specifically, blood flow 6 (as shown by an arrow) includes a vortex flow pattern originating in a superior aspect of the jugular bulb 3 and propagating down the descending jugular vein 4. It is believed that the blood flow 6, and in particular, its vortical shape, is a source of sound generation that is picked up by the cochlea and experienced by the patient as pulsatile tinnitus.

The present disclosure provides a method for treating pulsatile tinnitus by catheterizing the cerebral venous sinuses and implanting a device that removes or reduces the rotational component of blood flow without significantly disrupting the longitudinal component of the blood flow and/or the in-flow from adjacent cortical veins into the larger cerebral or cervical venous structure. Suitable implantable devices according to the present disclosure may be self-expanding or balloon expandable stents having one or more outer walls and one or more inner baffles disposed within a lumen defined by the outer wall.

The implantable devices may be constrained in a catheter, and when un-sheathed at the target location within the jugular vein or any other vascular location, self-expand so as to contact and push against the vessel walls to prevent migration of the device. In embodiments, the device may include one or more attachment members, e.g., hooks, anchors, or teeth, to embed the device in the venous wall. The outer walls of the implantable device are sufficiently permeable so as not to impede venous ingress from the cortical veins or internal jugular vein into the larger sinus. Thus, the device is minimally thrombogenic in order to minimize embolic risk to the systemic venous circulation and the pulmonary arterial system as a whole, since thrombogenicity could result in parent venous sinus occlusion. The permeability of the inner baffles of the device is low enough such that it sufficiently reduces and/or eliminates the rotational component of the vortex flow.

Figure 2:
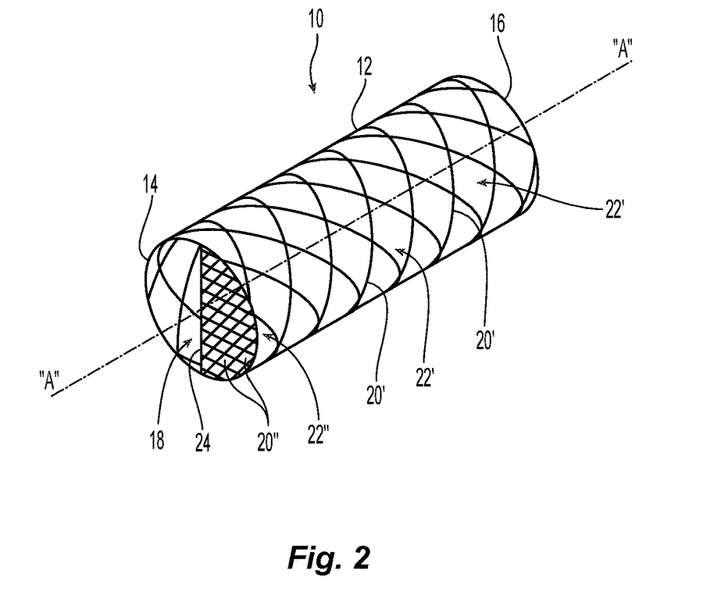
FIG. 2 is a perspective view of an implantable device according to one embodiment of the present disclosure.

With reference to FIG. 2, an implantable device for reducing and/or eliminating vortex flow is shown. The implantable device is shown as a tubular member 10 defining a longitudinal axis "A-A" and a lumen 18 extending along the longitudinal axis "A-A." The tubular member 10 includes an outer wall portion 12 and end portions 14 and 16. The outer wall portion 12 includes a plurality of interconnected strands 20' defining a plurality of openings 22' in between the interconnected strands 20'. The outer wall portion 12 is configured to contact the walls of a vessel such as, e.g., the jugular vein.

The tubular member 10 also includes an inner baffle portion 24 disposed within the lumen 18. The inner baffle portion 24 is coupled at one or more locations, e.g., edges, to the outer wall portion 12. The inner baffle portion 24 also includes a plurality of interconnected strands 20", which define a plurality of openings 22" therebetween. The inner baffle portion 24 is shown as a planar surface bisecting the lumen 18 of the tubular member 10. In embodiments, the inner baffle portion 24 may include a plurality of walls interconnected within the lumen 18, thus, separating the lumen 18 into any number of portions, e.g., sub-lumens.

The interconnected strands 20" forming the inner baffle portion 24 are spaced closer together than the interconnected strands 20' of the outer wall portion 12, such that the openings 22" of the inner baffle portion 24 are smaller than the openings 22' of the outer wall portion 12. Thus, the porosity of the inner baffle portion 24 is lower than the porosity of the outer wall portion 12. As used herein, the term "porosity" denotes a ratio between empty space defined by the openings 22'22" and space occupied by the interconnected strands 22'/22" forming the tubular member 10. This configuration, namely, a lower porosity of the inner baffle portion 24 and a higher porosity of the outer wall portion 12, disrupts the vortex flow pattern associated with pulsatile tinnitus while minimizing the effect on the longitudinal flow through the blood vessel.

Figure 3:
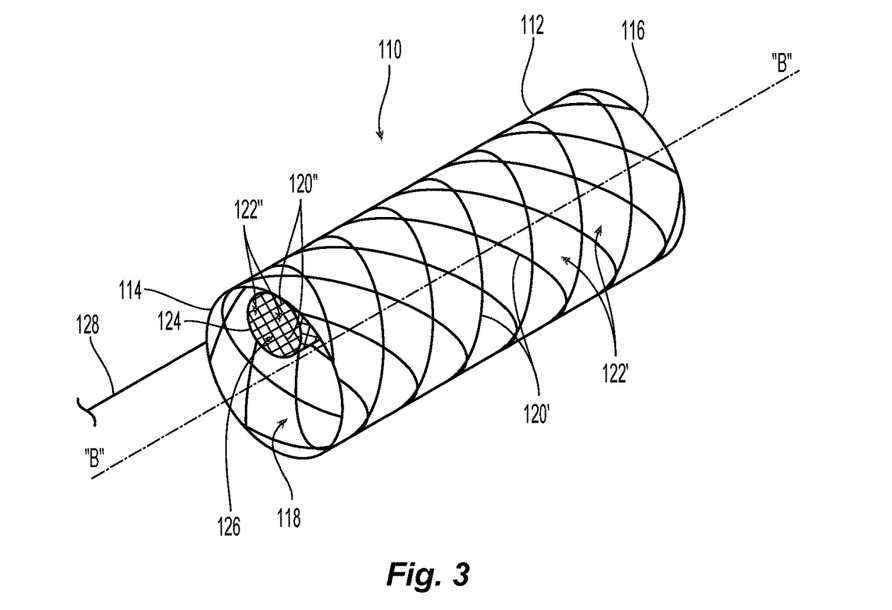
FIG. 3 is a perspective view of an implantable device according to another embodiment of the present disclosure.

With reference to FIG. 3, another embodiment of an implantable device according to the present disclosure is shown as a tubular member 110 defining a longitudinal axis "B-B" and a lumen 118. The tubular member 110 includes an outer wall portion 112 and end portions 114 and 116. The outer wall portion 112 also includes a plurality of interconnected strands 120' defining a plurality of openings 122' in between the interconnected strands 120'. The tubular member 110 also includes an inner baffle portion 124 disposed within the lumen 118. The inner baffle portion 124 is an inner tubular member coupled to an inner surface of the tubular member 110 along at least one edge of the inner baffle portion 124 and the outer wall portion 112. The inner baffle portion 124 may be eccentric (e.g., two circles that do not share the same center with one of the circles being contained within another circle) relative to the tubular member 110. The inner baffle portion 124 also defines an inner lumen 126, which is also eccentric with the lumen 118. In embodiments, the inner baffle portion 124 may be concentric with respect to the tubular member.

The inner baffle portion 124 also includes a plurality of interconnected strands 120" defining a plurality of openings 122". The interconnected strands 120" forming the inner baffle portion 124 are spaced closer together than the interconnected strands 120' of the outer wall portion 112, such that the openings 122" of the inner baffle portion 124 are smaller than the openings 122' of the outer wall portion 112. This configuration disrupts the vortex flow pattern associated with pulsatile tinnitus while minimizing effect on the longitudinal flow through the blood vessel similar to the tubular member 10 of FIG. 2

In embodiments, the inner baffle portion 124 may be connected to a wire 128 such that after implantation the diameter of the inner baffle portion 124 may be adjusted, which in turn, would adjust the porosity of the inner baffle portion 124. This is due to the constriction of the interconnected strands 120", thus, decreasing the size of the openings 122". Adjustment of the porosity of the inner baffle portion 124 allows for tuning its baffle effect on the rotational component of the blood flow. Since various blood vessels have different blood flow parameters and properties, it would be useful to tailor the porosity of the implantable device according to the properties of the blood flow.

Figure 4:
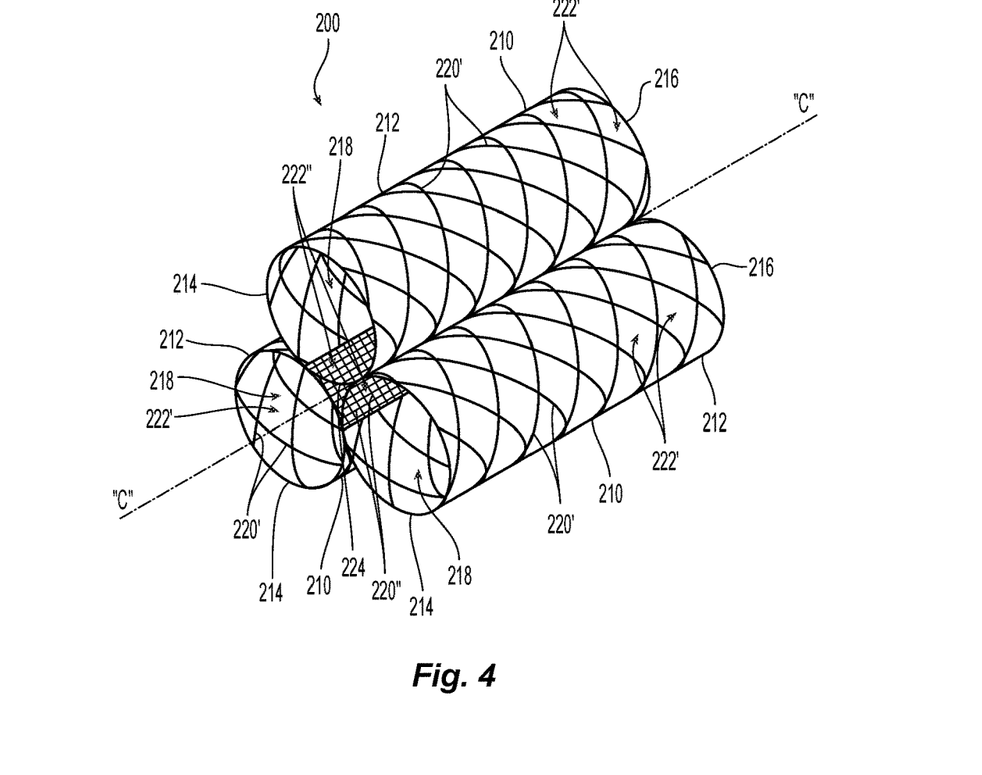
FIG. 4 is a perspective view of an implantable device according to yet another embodiment of the present disclosure.

With reference to FIG. 4, another embodiment of an implantable device according to the present disclosure is shown as an implantable device 200 having a plurality of tubular members 210 that are arranged in a stacked configuration and are parallel to a longitudinal axis "C-C." Each of the tubular members 210 includes an outer wall portion 212 and end portions 214 and 216 defining a lumen 218. Each of the tubular members 210 also includes an inner baffle portion 224. The outer wall portion 212 and the inner baffle portion 224 are formed on the same tubular member 210. However, when the tubular members 210 are joined together as shown in FIG. 4, the inner baffle portions 224 are disposed within the vessel lumen, whereas each of the outer wall portions 212 contacts the walls of the vessel.

Each of the outer wall portions 212 is formed by a plurality of interconnected strands 220' defining a plurality of openings 222' therebetween. In addition, each of the inner baffle portions 224 is formed by a plurality of interconnected strands 220" defining a plurality of openings 222". The interconnected strands 220" of the inner baffle portions 224 are spaced closer together than the interconnected strands 220' of the outer wall portions 212, such that the openings 222" of the inner baffle portions 224 are smaller than the openings 222' of the outer wall portions 212. Thus, the inner baffle portions 224 are less porous than the outer wall portions 212, which disrupts the vortex flow pattern associated with pulsatile tinnitus while minimizing the effect on the longitudinal flow through the blood vessel.

In embodiments, the porosity of the inner baffle portions 224 may be adjusted after implantation of the implantable device 200. This may be accomplished by varying a diameter of one or more of the tubular members 210. The diameter may be adjusted by using a balloon catheter, which is inserted into the lumen 218 of the tubular member 210 whose diameter is to be adjusted and the balloon is then inflated to increase the diameter. Increasing the diameter, in turn, increases the porosity of the outer wall portion 212 and the inner baffle portion 224 of the tubular member 210, while decreasing the porosity of the remaining tubular members 210 since all of the tubular members 210 are interconnected. Adjustment of the porosity of the inner baffle portions 224 allows for tuning its baffle effect on the rotational component of the blood flow. Since various blood vessels have different blood flow parameters and properties, it would be useful to tailor the porosity of the implantable device according to the properties of the blood flow.

Figure 5:
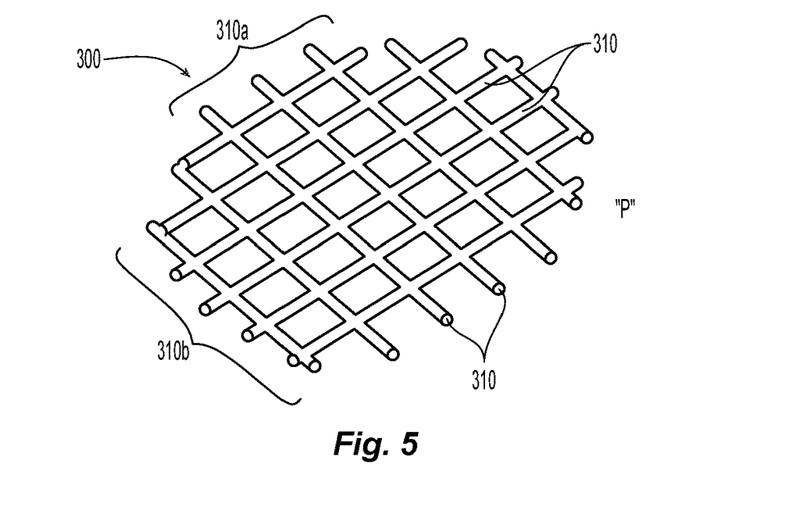
FIG. 5 is a perspective view of an implantable device according to a further embodiment of the present disclosure.

With reference to FIG. 5, another embodiment of an implantable device according to the present disclosure is shown as an implantable device 300 having a plurality of tubular members 310, which are arranged in a grid pattern thereby forming a mesh. The tubular members 310 may be substantially similar to the tubular members 10, 110, and 210 of FIGS. 2-4. The tubular members 310 may be disposed substantially in a plane "P." The implantable device 300 may include a first plurality 310a of tubular members 310 disposed in a first longitudinal axis and a second plurality 310b of tubular members 310 in a second longitudinal axis that is transverse to the first longitudinal axis, such that the first and second pluralities 310a and 310b intersect each other defining a plurality of openings 311. The tubular members 310 may be stents or stent struts and may have a diameter from about 0.1 mm to about 1.0 mm, in embodiments, from about 0.2 mm to about 0.6 mm. Since the tubular members 310 of the implantable device 300 are disposed in a single plane, the thickness of the implantable device 300 depends on the diameter of the tubular members 310 and may be from about 0.1 mm to about 1.0 mm, in embodiments, from about 0.2 mm to about 0.6 mm.

Each of tubular members 10, 110, 210, and 310 of FIGS. 2-5, respectively, may be self-expanding stents formed from a shape memory metal, such as a nickel-titanium alloy (nitinol) or shape memory polymers, such as those disclosed in U.S. Pat. No. 5,954,744, the entire disclosure of which is incorporated by reference herein. The stents may be machined or laser cut from a solid tube of material to form the interconnected strands according to the present disclosure.

In other embodiments, the tubular members 10, 110, 210, and 310 may be stents formed by braiding metal wire, polymer filaments, or combinations thereof, into desired shapes described above with respect to FIGS. 2-4. Either of the processes may be adjusted to form tubular members 10, 110, 210, and 310 having varying porosity as described above.

The tubular members 10, 110, 210, and 310 of FIGS. 2-5 may also include a plurality of attachment members, such as hooks, anchors, teeth, or other structures configured to grasp the walls of the blood vessel, such that the tubular members 10, 110, 210, and 310 are secured within vessel and to minimize migration of the tubular members 10, 110, 210, and 310 after implantation.

The tubular members 10, 110, 210, and 310 of FIGS. 2-5 may be delivered to the target vessels, e.g., cerebral or cervical veins, and in particular, to a location of maximal sound generation using any suitable transvenous surgical methods, which may include transfemoral, trans-torcular, or internal jugular vein access. Suitable delivery devices include balloon catheters and constrained stent delivery catheters depending on the type of tubular member 10, 110, 210, and 310 being used.

The tubular members 10, 110, and 210 may be implanted within the target vessels such that their longitudinal axes are substantially aligned with the blood flow or in alternative embodiments, such that their longitudinal axes are transverse relative to the blood flow. In other words, the tubular members 10, 110, and 210 may be implanted by attaching outer wall portions 12, 112, and 212 to the walls of the target vessels in order to align the longitudinal axes of the tubular members 10, 110, and 210 with the blood flow. In alternative embodiments, the tubular members 10, 110, and 210 may be implanted by attaching end portions 14, 16, 114, 116, 214, and 216 to the walls of the target vessels in order to place the tubular members 10, 110, and 210 across the target vessels and transverse with the blood flow.

Figure 6A:
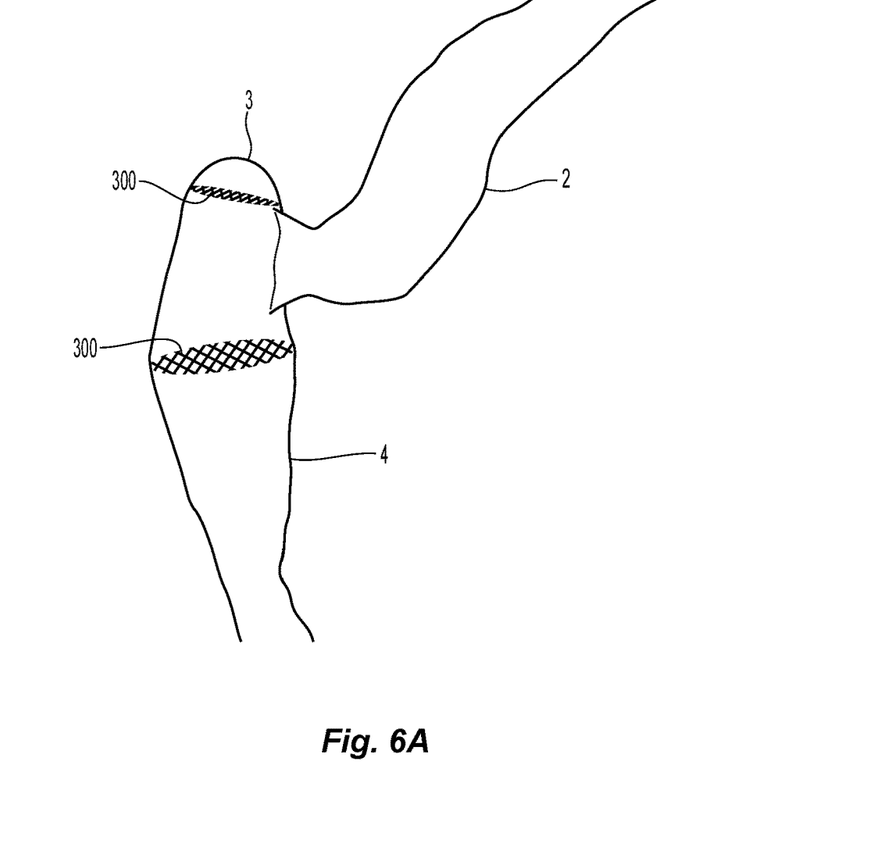
FIGS. 6A and 6B are three-dimensional images of a jugular vein and a jugular bulb each of which has an implantable device disposed therein.
Figure 6B:
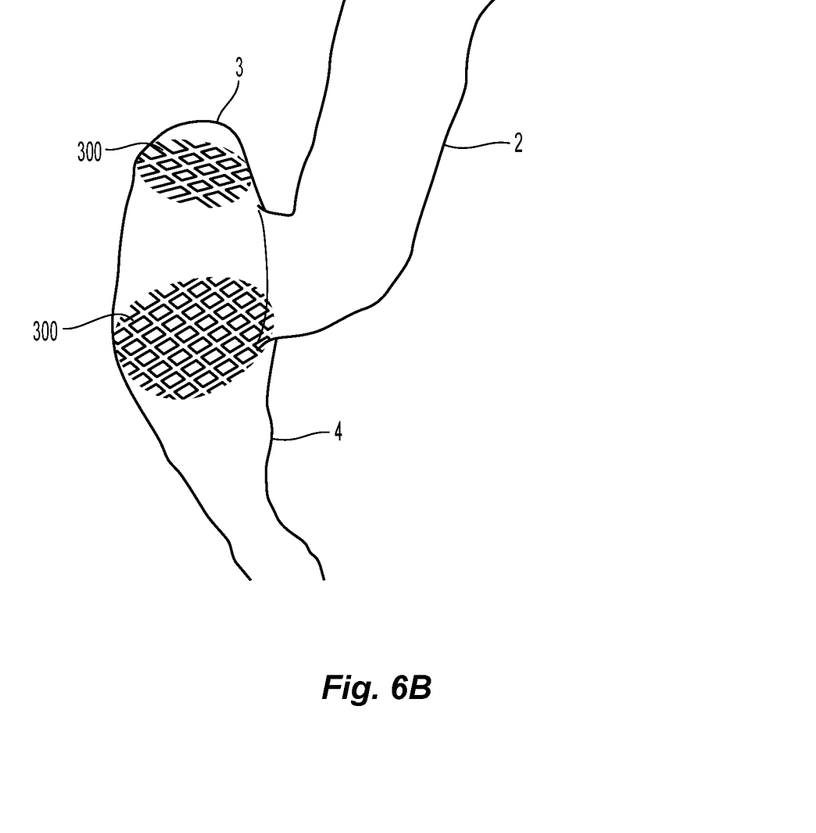

With reference to FIGS. 6A and 6B, implantable devices 300 are shown being implanted within the jugular bulb 3 and the jugular vein 4. In embodiments, the implantable devices 300 may be placed within the jugular bulb 3 and/or the jugular vein 4. The implantable devices 300 are implanted such that the plane "P" is transverse relative to the blood flow 6 (FIG. 1). In embodiments, the tubular members 10, 110, and 210 of FIGS. 2-4 may be also implanted at similar locations within the jugular bulb 3 and the jugular vein 4.

Figure 7A:
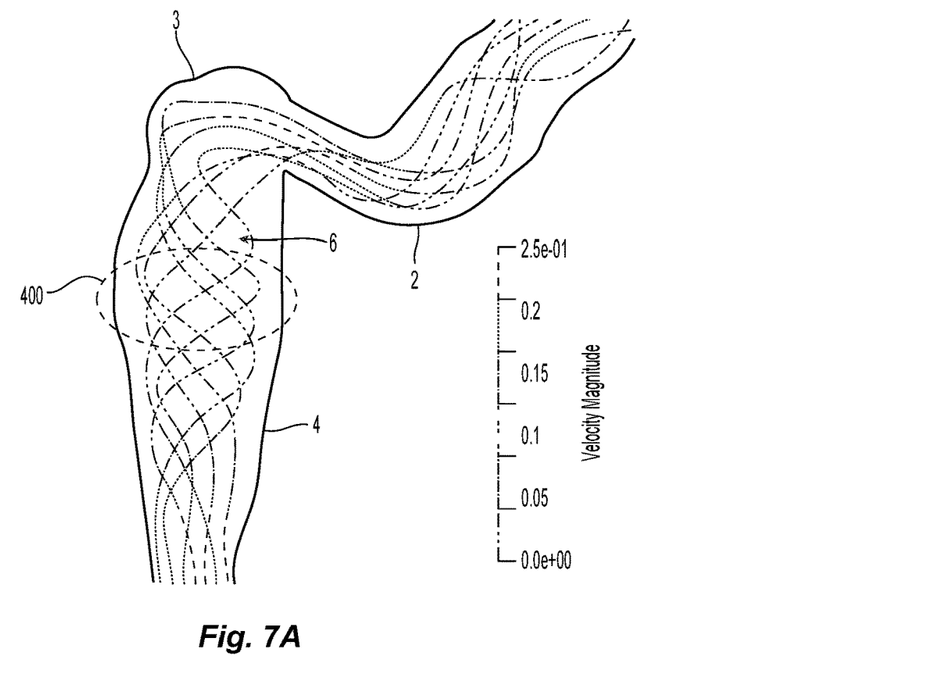
FIG. 7A is a three-dimensional velocimetry image of the jugular vein and the jugular bulb without the implantable devices of FIGS. 6A and 6B having a blood flow with a rotational component.

FIG. 7A shows the blood flow 6 from the sigmoid sinus 2, through jugular bulb 3, and the jugular vein 4. As illustrated in region 400, the blood flow 6 includes secondary flow features, such as rotational components, which result in vortex flow patterns. Thus, rather than having solely a primary flow component associated with the shape of jugular vein 4, e.g., along a y-axis, the blood flow 6 also includes secondary flow features, e.g., rotational components along an x-axis and a z-axis.

Figure 7B:
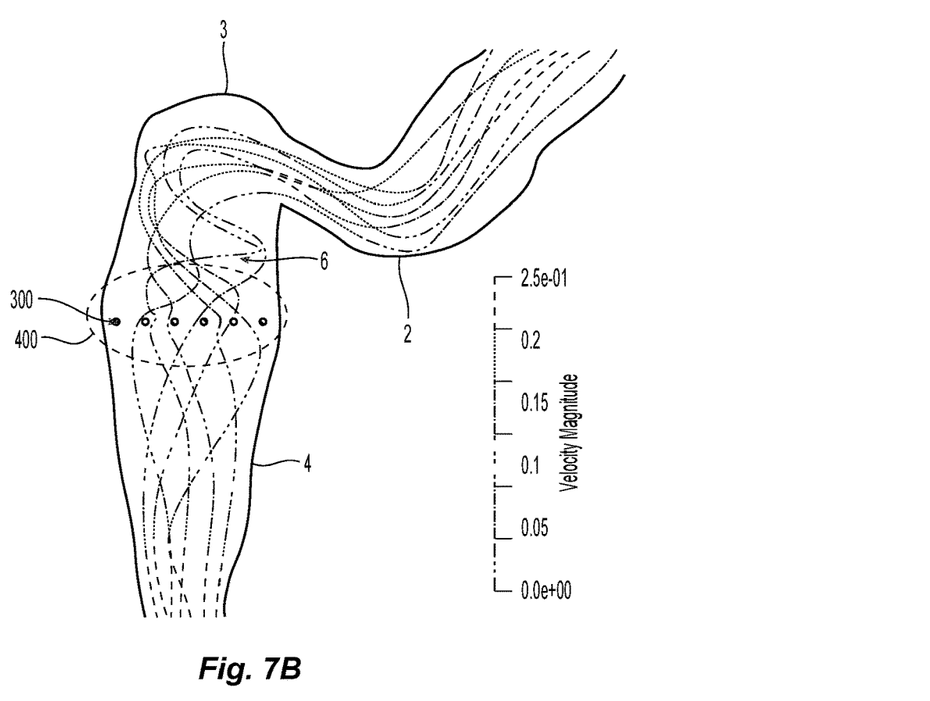
FIG. 7B is a three-dimensional velocimetry image of the jugular vein with the implantable device implanted therein illustrating a disruption of the rotational component of the blood flow.

FIG. 7B shows the blood flow 6 being disrupted by the implantable device 300, which is placed within the jugular vein 4. The blood flow 6 is changed after transiting through the implantable device 300, in that the secondary flow features are diminished as is illustrated by the flow pattern lines being more aligned with the jugular vein 4.

Figure 7C:
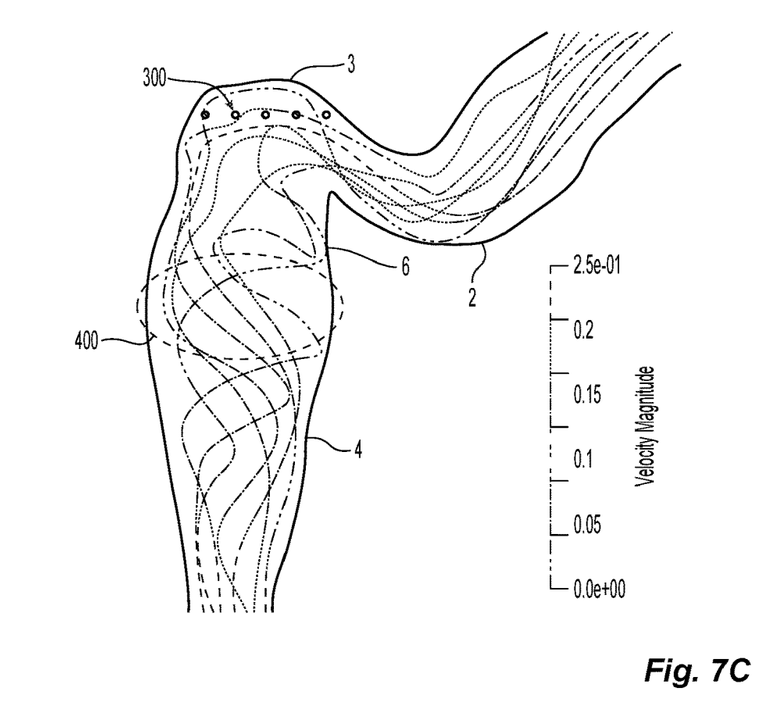
FIG. 7C is a three-dimensional velocimetry image of the jugular bulb with the implantable device implanted therein illustrating a disruption of the rotational component of the blood flow.

FIG. 7C shows the disruption in the blood flow 6 in response to the implantable device 300 being placed in the jugular bulb 3. Similarly, the blood flow 6 is modified after transiting through the implantable device 300. However, due to the placement of the implantable device 300 within the jugular bulb 3, the blood flow 6 is less organized than the blood flow 6 that is disrupted by the implantable device 300 that is implanted in the jugular vein 4 of FIG. 7B. As shown in FIG. 7C, the blood flow 6 retains some of its vortical shape, albeit it is less pronounced as compared to the blood flow 6 of FIG. 7A.

Figure 8A:
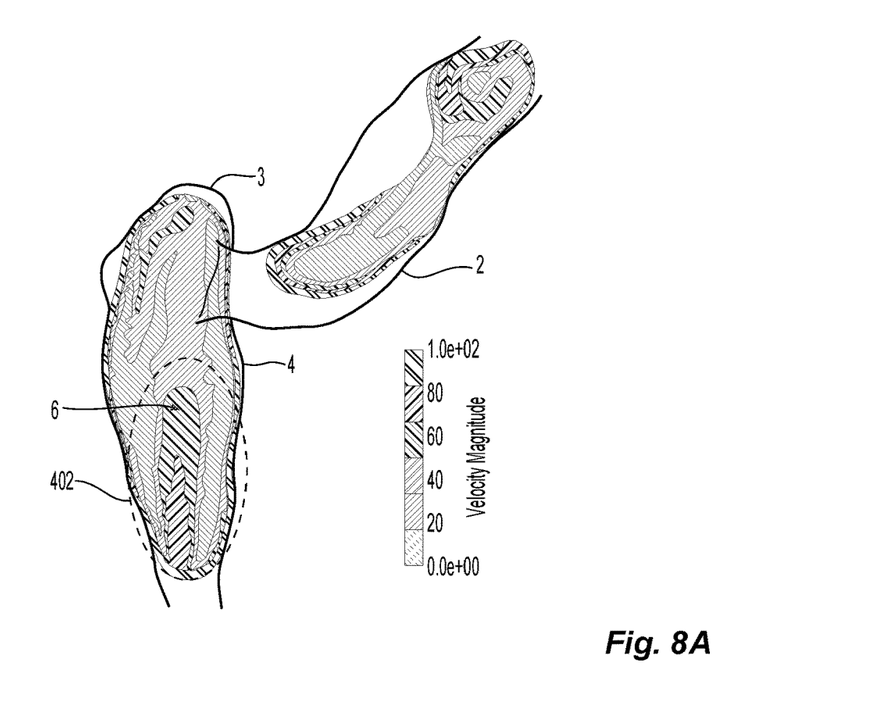
FIG. 8A is a two-dimensional velocimetry image, taken along a vertical plane, of the jugular vein and the jugular bulb without the implantable devices of FIGS. 6A and 6B having a blood flow with a rotational component.

FIG. 8A shows a cross-section taken along an x-y plane (FIG. 7A) of the blood flow 6 from the sigmoid sinus 2, through jugular bulb 3, and the jugular vein 4. As illustrated, the blood flow 6 has a higher velocity in a region 402 due to narrowing of the jugular vein.

Figure 8B:
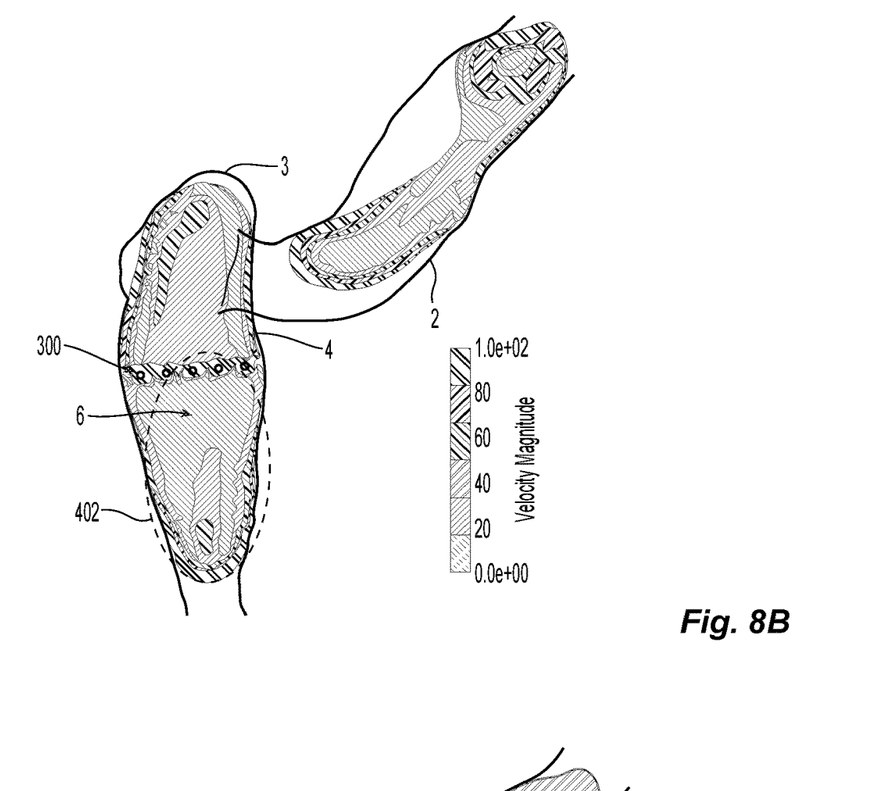
FIG. 8B is a two-dimensional velocimetry image, taken along a vertical plane, of the jugular vein with the implantable device implanted therein illustrating a disruption of the rotational component of the blood flow.

FIG. 8B, which like FIG. 7B, also shows the blood flow 6 being disrupted by the implantable device 300 placed within the jugular vein 4. The blood flow 6 is changed after transiting through the implantable device 300, in that the there is a reduction in the velocity of the primary flow component in the region 402. However, the velocity of the blood flow 6 is increased upstream of the implantable device 300, due to the constriction of the blood flow 6.

Figure 9A:
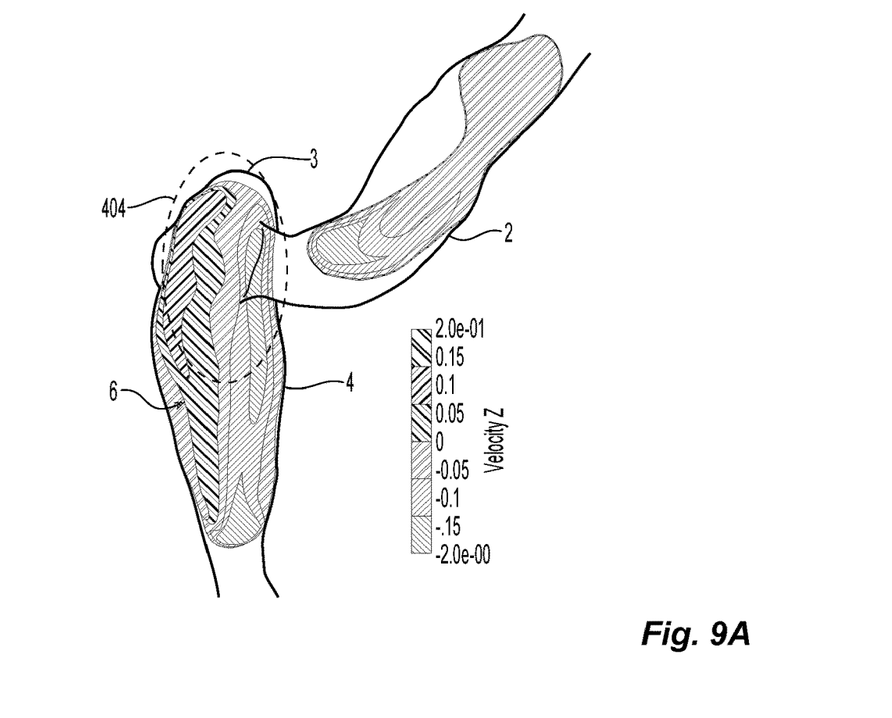
FIG. 9A is a two-dimensional velocimetry image, taken along a vertical plane, of the jugular vein and the jugular bulb without the implantable devices of FIGS. 6A and 6B having a blood flow with a rotational component.

FIG. 9A shows a cross-section taken along an x-y plane (FIG. 7A) of the blood flow 6 from the sigmoid sinus 2, through jugular bulb 3, and the jugular vein 4. As illustrated in region 404, the blood flow 6 includes secondary flow features, having a z-axis velocity component, which is oriented through the x-y plane. The region 404 extends from the jugular bulb 4 through the jugular vein 4.

Figure 9B:
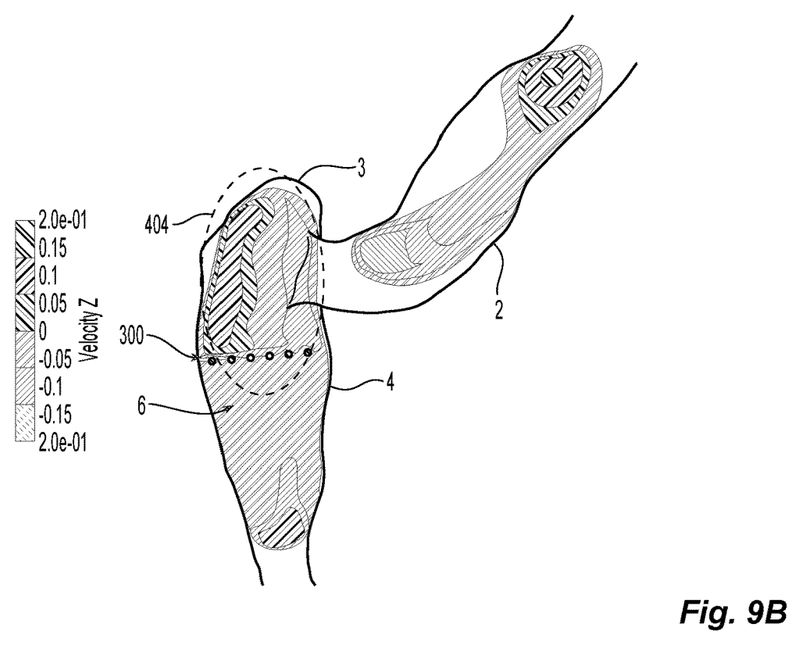
FIG. 9B is a two-dimensional velocimetry image, taken along a vertical plane, of the jugular vein with the implantable device implanted therein illustrating a disruption of the rotational component of the blood flow.

FIG. 9B shows the effect of implantable device 300, which is disposed within the jugular vein 4, on the blood flow 6 within the region 404. In particular, the downstream portion of the blood flow 6 of the region 404 is modified by the implantable device 300 by reducing the z-axis velocity component, whereas the upstream portion of the region 404 is unchanged.

Figure 9C:
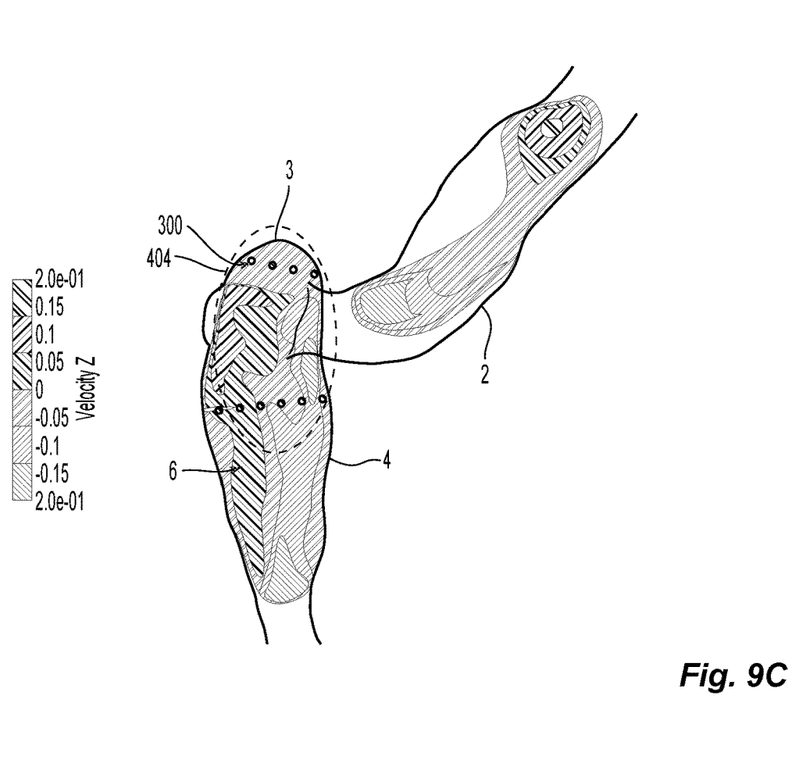
FIG. 9C is a two-dimensional velocimetry image, taken along a vertical plane, of the jugular bulb with the implantable device implanted therein illustrating a disruption of the rotational component of the blood flow.

FIG. 9C shows the effect of implantable device 300, which is disposed within the jugular bulb 3, on the blood flow 6 within the region 404. Similar to the disruption illustrated in FIG. 9B, the implantable device 300 within the jugular bulb 3 diminishes the z-axis velocity component of the blood flow 6 upstream of the implantable device 300, whereas the downstream portion of the region 404 is unchanged.

Figure 10A:
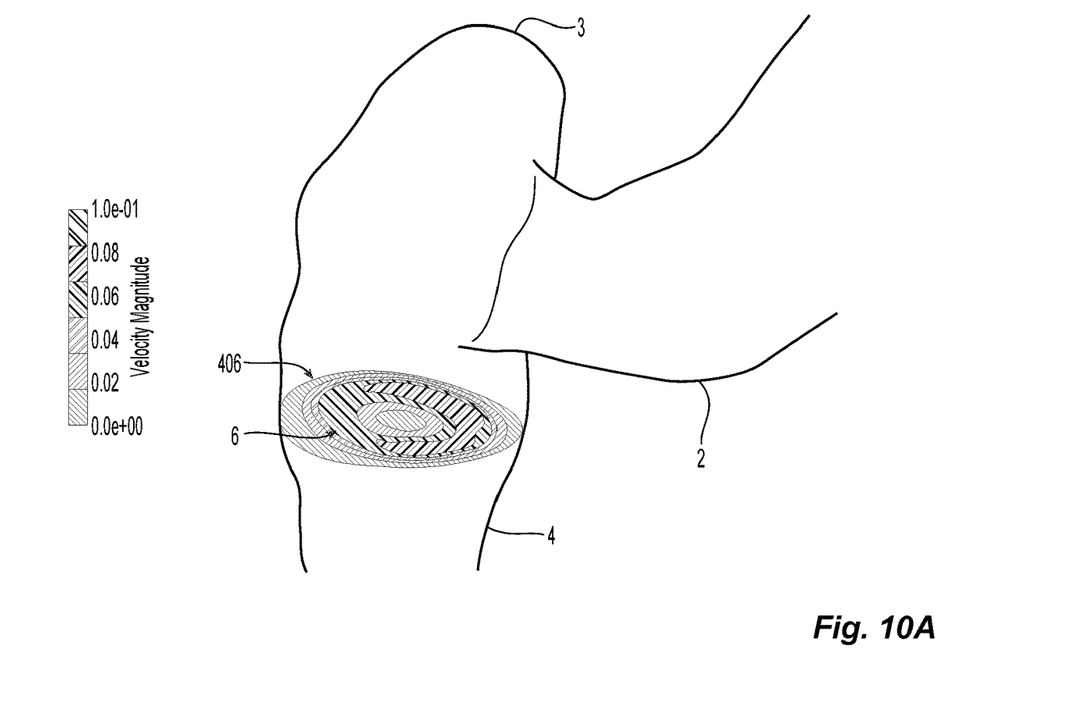
FIG. 10A is a two-dimensional velocimetry image, taken along a horizontal plane, of the jugular vein without the implantable devices of FIGS. 6A and 6B having a blood flow with a rotational component.
Figure 10B:
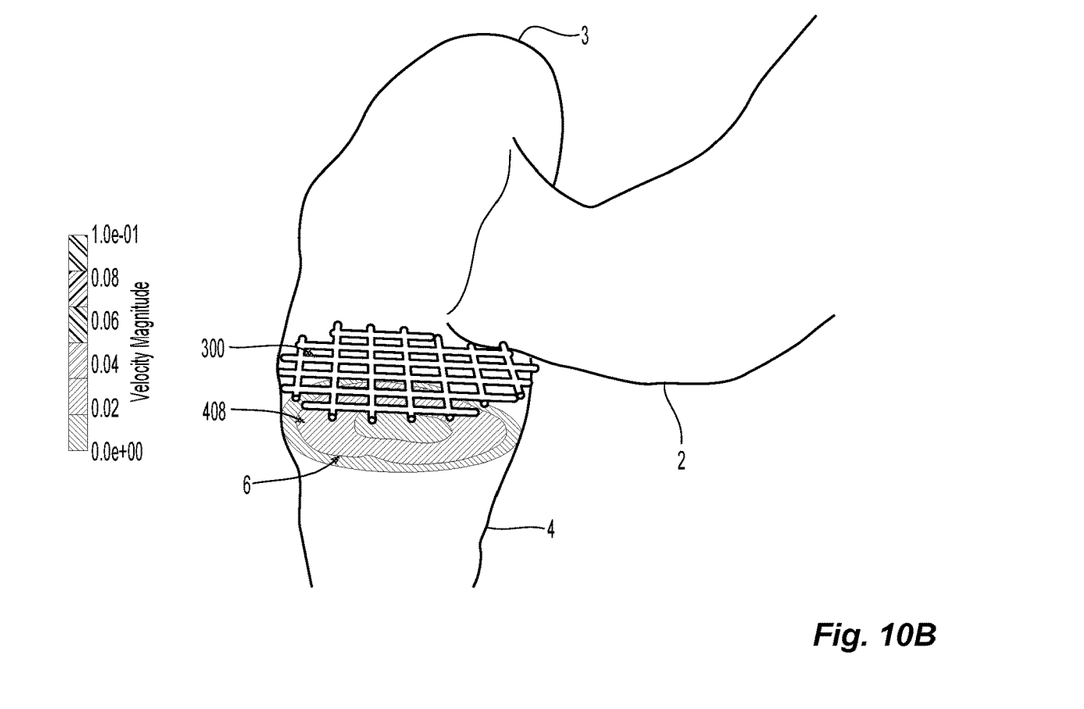
FIG. 10B is a two-dimensional velocimetry image, taken along a horizontal plane, of the jugular vein with the implantable device implanted therein illustrating a disruption of the rotational component of the blood flow.

FIG. 10A shows a cross-sectional velocimetry slice 406 of the blood flow 6 taken along an x-z plane (FIG. 7A). FIG. 10B shows the effect of the implantable device 300 being placed within the jugular vein 4. In particular, the implantable device 300 dampens the velocity of the blood flow 6, in this case the primary component of the blood flow 6 that is aligned with the jugular vein 4 as illustrated by a lower intensity of a velocimetry slice 408 in FIG. 10B.

Figure 11A:
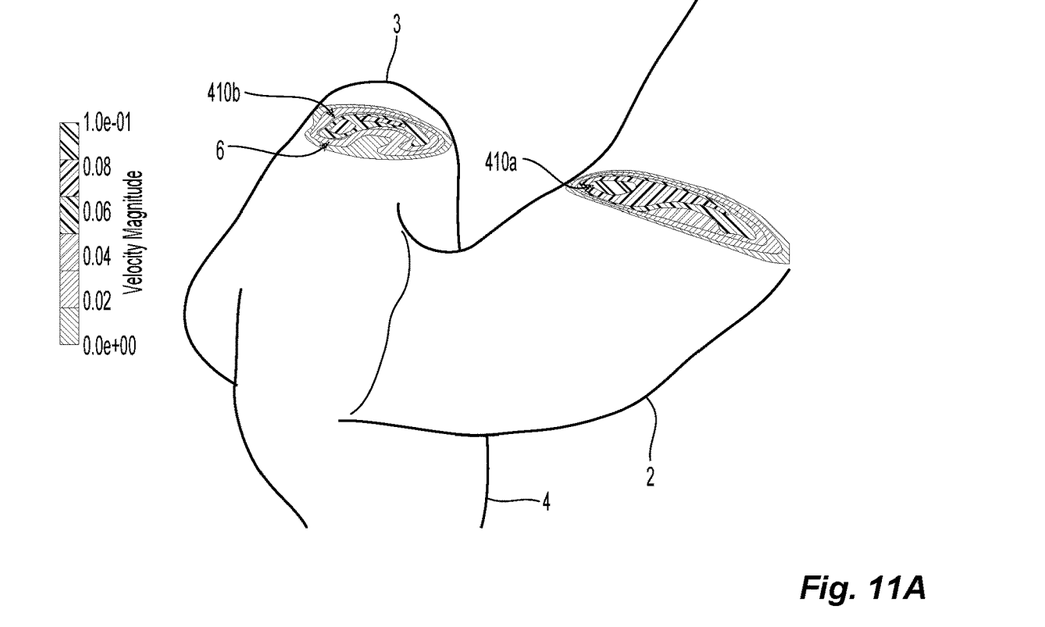
FIG. 11A is a two-dimensional velocimetry image, taken along a horizontal plane, of the jugular bulb and sigmoid sinus without the implantable devices of FIGS. 6A and 6B having a blood flow with a rotational component.
Figure 11B:
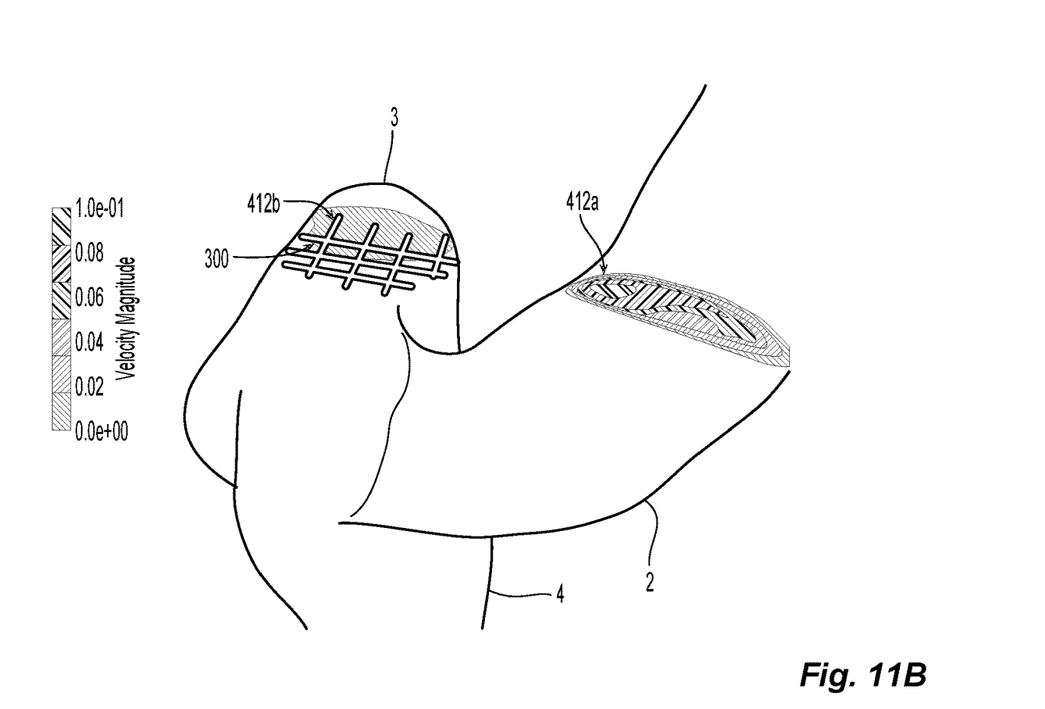
FIG. 11B is a two-dimensional velocimetry image, taken along a horizontal plane, of the jugular bulb with the implantable device implanted therein illustrating a disruption of the rotational component of the blood flow.

FIG. 11A shows a cross-sectional velocimetry slices 410*a* and 410*b* of the blood flow 6 taken along an x-z plane (FIG. 7A) within the sigmoid sinus 2 and the jugular bulb 3, respectively. FIG. 11B shows the effect of the implantable device 300 being placed within the jugular bulb 3. In particular, the implantable device 300 dampens the velocity of the blood flow 6, which in this case is the primary component of the blood flow 6 that is aligned with the jugular vein 4 as shown by a lower intensity of a velocimetry slice 412*b* of the jugular bulb 3 in FIG. 11B. However, the velocimetry slice 412*a* of the sigmoid sinus 2 is unaffected by the implantable device 300 due to its placement upstream of the implantable device 300.

In addition to causing pulsatile tinnitus, intravascular flow aberrations have been implicated in the development and progression of cerebral aneurysms, arteriovenous malformations, and stenoses in the great arteries of the head and neck, aorta and extremities, among others. Thus, the implantable devices according to the present disclosure can be implanted in various other vessels to treat pathologies that are responsive to modifying flow dynamics. Identifying and modifying the flow dynamics responsible for initial development of these pathologic states could result in arresting disease development at a very early stage, possibly before the anomaly is even visible. In patients where the disease has already begun, implanting devices to change the flow parameters could immediately modify the risk profile of the disease, serve as treatment for the disease, or at very least decrease the likelihood of progression of these diseases.

It will be understood that various modifications may be made to the embodiments disclosed herein. In particular, the implantable devices according to the present disclosure may be implanted in any suitable blood vessel where there is a need to modify and/or eliminate rotational component of the vortex blood flow. Therefore, the above description should not be construed as limiting, but merely as exemplifications of various embodiments. Those skilled in the art will envision other modifications within the scope and spirit of the claims appended thereto.

What is claimed is:

1. An implantable device comprising:
a plurality of outer tubular members, each of the outer tubular members defining a longitudinal axis and a lumen and including:
an outer wall portion having a plurality of first strands defining a plurality of first openings therebetween, the outer wall portion having a first porosity; and
an inner baffle portion, the inner baffle portion including a plurality of second strands defining a plurality of second openings therebetween, the inner baffle portion having a second porosity that is lower than the first porosity of the outer wall portion,
wherein each of the outer tubular members is joined to each other along their respective longitudinal axes.

2. The implantable device according to claim 1, wherein at least one of the first porosity and the second porosity are adjustable.

3. The implantable device according to claim 1, wherein the outer tubular members are arranged in a stacked configuration.

4. The implantable device according to claim 1, wherein each of the outer tubular members are in contact with each other.

5. The implantable device according to claim 1, wherein the outer tubular members are arranged in a parallel configuration such that each of the longitudinal axes are parallel to each other.

6. The implantable device according to claim 1, wherein the outer tubular members are arranged such that the inner baffle portions are facing each other and the outer wall portions of the outer tubular members are facing outward and contact a blood vessel.

7. The implantable device according to claim 6, wherein the inner baffle portions are configured to disrupt blood flow of the blood vessel.

\* \* \* \* \*